United States Patent [19]

Kahan et al.

[11] 4,264,734
[45] Apr. 28, 1981

[54] PROCESS FOR PRODUCING ANTIBIOTIC DESACETYL $890A_{10}$

[75] Inventors: Jean S. Kahan; Frederick M. Kahan, both of Rahway, N.J.

[73] Assignee: Merck & Co., Inc., Rahway, N.J.

[21] Appl. No.: 74,289

[22] Filed: Sep. 11, 1979

Related U.S. Application Data

[63] Continuation of Ser. No. 860,665, Dec. 15, 1977, abandoned, which is a continuation of Ser. No. 767,223, Feb. 11, 1977, abandoned.

[51] Int. Cl.³ ............................................. C12P 17/18
[52] U.S. Cl. .................................... 435/119; 435/822; 435/228
[58] Field of Search .......................... 435/119, 44, 228

[56] References Cited

U.S. PATENT DOCUMENTS

| 3,446,705 | 5/1969 | Heuser et al. | 435/44 |
| 3,962,036 | 6/1976 | Liensch et al. | 435/228 |
| 4,113,856 | 9/1978 | Cole et al. | 435/119 |

Primary Examiner—Alvin E. Tanenholtz
Attorney, Agent, or Firm—Frank M. Mahon; Julian S. Levitt

[57] ABSTRACT

This invention relates to the new antibiotic, desacetyl $890A_{10}$, active against both gram-positive and gram-negative bacteria, which is produced by treating $890A_{10}$ with an N-acetyl-$890A_{10}$ amidohydrolase produced by a soil microorganism isolated by enrichment techniques. This invention also relates to the process by which $890A_{10}$ is enzymatically deacetylated.

2 Claims, No Drawings

PROCESS FOR PRODUCING ANTIBIOTIC DESACETYL 890A$_{10}$

This is a continuation of application Ser. No. 860,665, filed Dec. 15, 1977, now abandoned, which in turn is a continuation of application Ser. No. 767,223, filed Feb. 11, 1977, now abandoned.

BACKGROUND OF THE INVENTION

The discovery of the remarkable antibiotic properties of penicillin stimulated great interest in this field which has resulted in the finding of many other valuable antibiotic substances such as: other penicillins, streptomycin, bacitracin, tetracyclines, chloramphenicol, erythromycins and the like. In general, the antibacterial activity of each of these antibiotics does not include certain clinically important pathogenic bacteria. For example, some are principally active against only gram-positive types of bacteria. Acquired resistance over the course of widespread use of existing antibiotics in the treatment of bacterial infection has caused a serious resistance problem to arise.

Accordingly, the deficiencies of the known antibiotics have stimulated further research to find other antibiotics which will be active against a wider range of pathogens as well as resistant strains of particular microorganisms.

SUMMARY OF THE INVENTION

This invention relates to a new antibiotic agent. More particularly, it is concerned with the new antibiotic substance, herein called desacetyl 890A$_{10}$. The invention encompasses the antibiotic in dilute forms, as crude concentrates and in pure forms.

It is an object of the present invention to provide the new and useful antibiotic which is highly effective in inhibiting the growth of various gram-negative and gram-positive microorganisms. Another object is to provide a process for the preparation of this novel antibiotic substance by the enzymatic deacetylation of the compound 890A$_{10}$. Other objects will be apparent from the detailed description of this invention hereinafter provided.

The novel antibiotic substance of the present invention is produced by hydrolyzing the N-acetyl group of 890A$_{10}$ using an amidohydrolase capable of hydrolyzing the N-acetyl group. A convenient source of an amidohydrolase with this capability is amidohydrolase producing strains of the microorganism *Protaminobacter ruber*. The particular enzyme produced by *Protaminobacter ruber* is N-acetyl-890A$_{10}$ amidohydrolase, a member of the sub-group of enzymes designated E.C. 3.5.1 according to the recommended enzyme nomenclature of the International Union of Pure and Applied Chemistry and the International Union of Biochemistry.

The microorganism capable of carrying out the deacetylation process was isolated from a soil sample and, based upon taxonomic studies, was identified as belonging to the species *Protaminobacter ruber* and has been designated MB-3528 in the culture collection of MERCK & CO., Inc., Rahway, N.J. A culture thereof has been placed on unrestricted permanent deposit with the culture collection of the Northern Regional Research Laboratories, Northern Utilization Research and Development Division, Agricultural Research Service, U.S. Department of Agriculture, Peoria, Ill., and has been assigned accession No. NRRL B-8143.

The morphological and cultural characteristics of *Protaminobacter ruber* NRRL B-8143 as well as carbon and nitrogen utilization and biochemical reactions are as follows:

MORPHOLOGY

Cells are rod-shaped with rounded ends, 0.9–1.2×2-.3–4.6 microns, occurring singly or in pairs. Twenty-four and forty-eight hour cells stain gram-negative with a granular appearance. The granules, especially the polar granules, stain black with Sudan Black B. Cells are motile at 28° C., but motility is questionable at 37° C.

CULTURAL CHARACTERISTICS

Nutrient agar colonies are at first thin, punctiform, semi-transparent and colorless; then becoming low convex, opaque, smooth, edge entire, somewhat dry in consistency and pigmented rose to rose-red.

Nutrient broth cultures are uniformly turbid with no pellicle.

Pigment production is not dependent on light or temperatures tested (28° C. and 37° C.). Pigment is soluble in acetone but insoluble in water or chloroform.

Growth on nutrient agar and brain-heart infusion agar under aerobic conditions is somewhat slow but good at 28° C.; growth is moderate to good but slower at 37° C.; there is no growth at 50° C.

UTILIZATION OF CARBON AND NITROGEN SOURCES

Using a basal salts medium with ammonium sulfate as nitrogen source, growth is good with arabinose, moderate with xylose, and poor with dextrose, fructose, mannose, rhamnose, lactose, maltose, sucrose, raffinose, cellulose, inositol and mannitol.

N-acetylethanolamine can be utilized as the sole carbon and nitrogen source.

No acid or gas is produced from dextrose or lactose in OF Basal Medium (Difco Laboratories, Detroit, Mich.) under aerobic or anaerobic conditions.

BIOCHEMICAL REACTIONS

The biochemical reactions are based on standard methods as described in *Manual of Microbiological Methods*, edited by the Society of American Bacteriologists, McGraw-Hill Book Co., New York, 1957.

Catalase—positive
Oxidase—negative
Starch not hydrolyzed
Casein not hydrolyzed
Gelatin not liquefied
Litmus milk unchanged in consistency but becomes slightly alkaline after 7 days.
Indol—negative
H$_2$S—negative
Nitrates not reduced
Urease—positive
Lysine and ornithine decarboxylase—negative.

890A$_{10}$ is the term applied to the antibiotic having the structure:

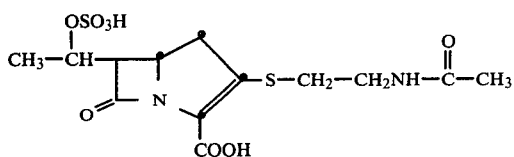

890A$_{10}$, its description and processes of production are set forth in the application of Cassidy et al., U.S. Ser. No. 742,958, filed Nov. 17, 1976 which is herein incorporated by reference.

The novel antibiotic of the present invention, desacetyl 890A$_{10}$ has the structural formula:

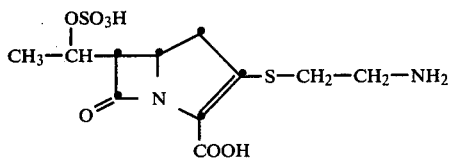

and is prepared by enzymatic hydrolysis of 890A$_{10}$, using an amidohydrolase present in species of genus Protaminobacter.

The novel process of the present invention relates to the cleavage of the N-acetyl group of the compound of the structure:

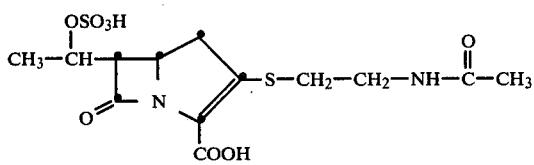

which comprises intimately contacting said compound with an amidohydrolase capable of hydrolyzing the N-acetyl group. More specifically, the process of the present invention provides for the N-deacetylation of 890A$_{10}$ by intimately contacting said compound with the amidohydrolase, N-acetyl-890A$_{10}$ amidohydrolase.

An unexpected homology between N-acetylethanolamine and 890A$_{10}$ is set forth, whereby extracts of microorganisms with the enzyme, N-acetylethanolamine amidohydrolase, are in many cases able to hydrolyze 890A$_{10}$.

The compound 890A$_{10}$ is prepared by the fermentation of broth with the microorganism *Streptomyces flavogriseus*.

Based upon extensive taxonomic studies, the strain of microorganism used in the present invention was identified as belonging to the species *Streptomyces flavogriseus* and has been designated MA-4638 in the culture collection of MERCK & CO., Inc., Rahway, N.J. A culture thereof has been placed on permanent deposit without restrictions as to availability with the culture collection of the Northern Regional Laboratories, Northern Utilization Research and Development Division, Agricultural Research Service, U.S. Department of Agriculture, Peoria, Ill., and is available to the public under accession No. NRRL 11,020.

*Streptomyces flavogriseus* MA-4638 produces antibiotic 890A$_{10}$ which is isolated in substantially pure form from the fermentation broth.

The morphological and cultural characteristics of *Streptomyces flavogriseus* MA-4638 are set forth in the following table.

MORPHOLOGY

Sporophores are branching, straight to flexuous chains of spores, forming tufts. Chains are more than 10 spores in length. Spores are spherical to oval—0.9$\mu \times$ 1.2$\mu$(970x).

CULTURAL CHARACTERISTICS

Oatmeal agar (ISP Medium 3)

Vegetative growth—Reverse-yellow-tan edged with brown, wrinkled;
Aerial mycelium—Light gray edged with medium gray
Soluble pigment—None.

Czapek Dox agar (sucrose nitrate agar)

Vegetative growth—Reverse-brown edged with dark brown;
Aerial mycelium—Medium gray, velvety;
Soluble pigment—Slight browning of medium.

Egg albumin agar

Vegetative growth—Reverse-yellow-tan edged with brown;
Aerial mycelium—Medium gray mixed with yellowish gray (2dc) and grayed yellow (2db);
Soluble pigment—Light yellowish tan.

Glycerol asparagine agar

Vegetative growth—Reverse-brown;
Aerial mycelium—Velvety, light gray with yellowish tone (2dc);
Soluble pigment—Light tan.

Inorganic salts-starch agar (ISP Medium 4)

Vegetative growth—Reverse-greenish-yellowish-tan;
Aerial mycelium—velvety, medium gray with yellow tone (3fe);
Soluble pigment—Very light tan.

Yeast extract-dextrose+salts agar

Vegetative growth—Reverse-dark brown;
Aerial mycelium—Dark gray mixed with a lighter gray;
Soluble pigment—None.

Yeast extract-malt extract agar (ISP Medium 2)

Vegetative growth—Reverse-brown;
Aerial mycelium—Velvety, dark gray edged with a lighter gray;
Soluble pigment—None.

Skim milk agar

Vegetative growth—Tan;
Aerial mycelium—Sparse, whitish;
Soluble pigment—Slight browning of medium;
Hydrolysis of casein—Good.

Litmus milk

Vegetative growth—Moderate growth ring, tan;
Aerial mycelium—None;
Color—Purple;
Coagulation and/or peptonization—Complete peptonization; becoming alkaline.

Skim milk

Vegetative growth—Moderate growth ring, tan;
Aerial mycelium—None;
Soluble pigment—Light brown;
Coagulation and/or peptonization—Complete peptonization; becoming alkaline.

Nutrient tyrosine agar

Vegetative growth—Reverse-dark brown;
Aerial mycelium—Dark gray edged with grayish white;
Soluble pigment—Slight browning of medium;
Decomposition of tyrosine—Positive.

Peptone-iron-yeast extract agar

Vegetative growth—Tan;
Aerial mycelium—whitish, moderate;
Soluble pigment—None;
Melanin—None;
$H_2S$ production—Negative.

Nutrient agar

Vegetative growth—Reverse-light grayish brown;
Aerial mycelium—Light gray edged with dark gray;
Soluble pigment—None.

Nutrient starch agar

Vegetative growth—Tan edged with gray;
Aerial mycelium—Medium gray;
Soluble pigment—None;
Hydrolysis of starch—Good.

Nutrient gelatin agar

Vegetative growth—Tan edged with gray;
Aerial mycelium—Grayish-white;
Soluble pigment—None;
Liquefaction of gelatin—Good.

Potato plug

Vegetative growth—Tan;
Aerial mycelium—Medium to dark gray;
Soluble pigment—None.

Loeffler's Blood serum

Vegetative growth—Cream-colored;
Aerial mycelium—None;
Soluble pigment—None;
Liquefaction—None.

Gelatin stabs

Vegetative growth—Tan;
Aerial mycelium—None;
Soluble pigment—None;
Liquefaction of gelatin—Complete.

All of the readings reported above were taken after three weeks incubation at 28° C. unless noted otherwise. The pH of the media used in these studies was approximately neutral, namely, pH 6.8–7.2. The color designations used in the description are in accordance with the definitions of the *Color Harmony Manual,* 4th Edition (1958), Container Corporation of America, Chicago, Ill.

*Streptomyces flavogriseus* MA-4638 was also tested for its ability to utilize or assimilate various carbohydrates. For this purpose, the microorganism was grown on basal synthetic medium (Pridham and Gottlieb) containing 1% of the carbohydrate at 28° C. for three weeks. The pH of the media employed in the study was approximately neutral (6.8–7.2). Table I shows the utilization of these carbohydrate sources by *Streptomyces flavogriseus* MA-4638; +indicating growth, ±poor or questionable growth, and −no growth as compared to negative control (no carbon source).

TABLE I

| Glucose | + | Maltose | + |
|---|---|---|---|
| Arabinose | + | Mannitol | + |
| Cellulose | − | Mannose | + |
| Fructose | + | Raffinose | − |
| Inositol | − | Rhamnose | + |
| Lactose | + | Sucrose | ± |
| Xylose | + | | |

The amount of growth with change in temperature and the oxygen requirement by the microorganism is as follows:

Temperature range (Yeast extract-dextrose+salts agar);
28° C.—Good vegetative and aerial growth
37° C.—Good vegetative growth; no aerial hyphae
50° C.—No growth Oxygen requirement (Stab culture in yeast extract-dextrose+salts agar);
Aerobic The present invention is not limited to the organism, *Streptomyces flavogriseus* or to organisms fully answering the above growth and microscopic characteristics which are given for illustrative purposes. It is desired and intended to include the use of mutants produced from the described organism by various means, such as X-radiation, ultraviolet radiation, nitrogen mustard, phage exposure and the like.

890A$_{10}$ is produced during the aerobic fermentation, under controlled conditions, of suitable aqueous nutrient media inoculated with a strain of the organism, *Streptomyces flavogriseus.* Aqueous media, such as those employed for the production of other antibiotics, are suitable for producing 890A$_{10}$. Such media contain sources of carbon, nitrogen and inorganic salts assimilable by the microorganism.

In general, carbohydrates such as sugars, for example, dextrose, glucose, fructose, maltose, sucrose, xylose, mannitol and the like and starches such as dextrin or such as grains, for example, oats, rye, cornstarch, corn meal and the like can be used either alone or in combination as sources of assimilable carbon in the nutrient medium. The amount of carbohydrate usually varies between about 1% and 6% by weight of the medium. These carbon sources can be used individually, or several such carbon sources may be combined in the medium. In general, many proteinaceous materials may be used as nitrogen sources in the fermentation process. Suitable nitrogen sources include, for example, yeast hydrolysates, primary yeast, soybean meal, cottonseed flour, hydrolysates of casein, corn steep liquor, distiller's solubles or the like, the preferred source being distiller's solubles. The sources of nitrogen, either alone or in combination, are used in amounts ranging from about 0.2% to 6% by weight of the aqueous medium.

Among the nutrient inorganic salts which can be incorporated in the culture media are the customary salts capable of yielding sodium, potassium, ammonium, calcium, magnesium, phosphate, sulfate, chloride, carbonate, and like ions. Also included are trace metals such as cobalt, manganese and iron.

The media described in the Examples are merely illustrative of the wide variety of media which may be employed, and are not intended to be limitative.

The fermentation is carried out at temperatures ranging from about 20° C. to 37° C.; however, for optimum results it is preferable to conduct the fermentation at temperatures of from about 23° C. to 28° C. The initial pH of the nutrient media suitable for growing strains of the *Streptomyces flavogriseus* culture and producing antibiotic 890A$_{10}$ can vary from about 6.0 to 8.0.

Although the antibiotic 890A$_{10}$ is produced by both surface and submerged cultures, it is preferred to carry out the fermentation in the submerged state.

A small scale fermentation of the antibiotic is conveniently carried out by inoculating a suitable nutrient medium with the antibiotic-producing culture and, after transfer to a production medium, permitting the fermentation to proceed at a constant temperature of about 24° C. on a shaker for several days.

The fermentation is initiated in a sterilized flask of nutrient medium via one or more stages of seed development. The nutrient medium for the seed stage may be any suitable combination of carbon and nitrogen sources. The seed flask is shaken in a constant temperature chamber at about 28° C. for one day, or until growth is satisfactory, and some of the resulting growth is used to inoculate either a second stage seed or the production medium. Intermediate stage seed flasks, when used, are developed in essentially the same manner; that is, part of the contents of the flask from the last seed stage are used to inoculate the production medium. The inoculated flasks are shaken at a constant temperature for several days, and at the end of the incubation period the contents of the flask are centrifuged or filtered.

For large scale work, it is preferable to conduct the fermentation in suitable tanks provided with an agitator and a means for aerating the fermentation medium. According to this method, the nutrient medium is made up in the tank and sterilized by heating at temperatures of up to about 120° C. Upon cooling, the sterilized medium is inoculated with a previously grown seed of the producing culture, and the fermentation is permitted to proceed for a period of time as, for example, from 1 to 6 days while agitating and/or aerating the nutrient medium and maintaining the temperature at about 22° to 26° C. This method of producing antibiotic 890A$_{10}$ is particularly suited for the preparation of large quantities of the antibiotic.

PHYSICAL AND CHEMICAL PROPERTIES OF ANTIBIOTIC 890A$_{10}$

Antibiotic 890A$_{10}$ is an acidic substance which migrates toward the positive pole on electrophoresis at neutral pH. At a gradient of 50 volts/cm. in 0.03 M potassium phosphate buffer, pH 7.1, the antibiotic moves 8.0 cm. in 30 minutes, compared with movement of 4.0 cm. for 890A$_1$. The disodium salt is a white or slightly yellow powder as lyophilized from aqueous solution. Under acidic conditions in aqueous solution, the antibiotic is unstable, and the free acid form has not been isolated.

The disodium salt of antibiotic 890A$_{10}$ has an absorption maximum at 299 nm and a minimum at 243 nm at neutral pH in water. The E% at 300 nm of the most highly purified preparation of disodium salt is 214. The ratio $A_{300}/A_{250}$ is 3.33 for the most purified sample, and the ratio $A_{300}/A_{220}$ is 2.05. Evidence of slight impurities in this sample suggests that the corresponding ratios for a sample of ultimate purity would be somewhat higher. More than 94% of the absorption at 300 nm can be extinguished by reaction with hydroxylamine at neutral pH. The absorbance at 250 nm also decreases upon reaction with hydroxylamine, and the ratio of the absorbance decrease at 250 nm to the decrease at 300 nm, is approximately 0.16. The reaction with hydroxylamine, as followed by $A_{300}$ decrease under the conditions described in the section "Hydroxylamine Reaction" is apparently first order, with a half-life at room temperature of from 23 to 60 seconds.

When measured against a standard of antibiotic 890A$_1$, the antibiotic 890A$_{10}$ has 174 bioassay units per HAEA$_{300}$ unit. HAEA$_{300}$ is described under the section "Hydroxylamine Reaction".

Table II lists the 100 MHz-nuclear magnetic resonance spectral signal of 890A$_{10}$ in D$_2$O at 32° C. Chemical shifts are given in ppm relative to HOD at 4.70Δ at 32° C., and coupling constants in Hertz.

TABLE II

| | |
|---|---|
| CH$_3$CH | 1.55 (3H;d;6.5 Hz) |
| CH$_3$CO | 2.02 (3H; s) |
| C$_{(6)}$—H | 3.89 (1H;d,d;J$_{6-5}$ = 5.4 Hz;J$_{6-8}$ = 9.2 Hz) |
| C$_{(5)}$—H | ~4.34 (1H;d,t;J$_{5-6}$ = 5.5 Hz;J$_{5-1}$ = 9.5 Hz) |
| C$_{(8)}$—H | ~4.8 (partially covered by HOD line) |
| C$_{(1)}$—H$_2$ | ~3.14 (1H;d,d;~9.2 + ~18 Hz) |
| | ~3.33 (1H;d,d;~10 + 18 Hz) |
| —CH$_2$NH | 3.43 (2H;t;7Hz) |
| —CH$_2$—S— | 3.03 (2H,m) |

The mass spectra of TMSi-890A$_{10}$ is characterized by fragments as shown in Table III.

TABLE III

| m/e | | |
|---|---|---|
| | 86 | |
| | 227.0224 | C$_5$H$_{15}$SO$_4$Si$_2$, calc. 227.0230 |
| | 241 | |
| | 300/1 | |
| | 339.1325 | C$_{15}$H$_{25}$NO$_4$Si$_2$, calc. 339.1322 |
| | 342.1444 | C$_{15}$H$_{26}$N$_2$O$_3$S Si, calc. 342.1433 |
| | 368 | |
| | 440 | |
| | 458 | |

Antibiotic 890A$_{10}$ has a molecular structure as follows:

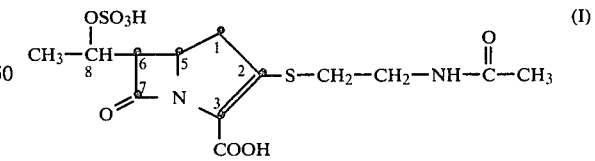

Desacetyl 890A$_{10}$, the compound of this invention is a valuable antibiotic active against various gram-positive and gram-negative bacteria and, accordingly, finds utility in human and veterinary medicine. The compound of this invention can be used as an antibacterial drug for treating infections caused by gram-positive or gram-negative bacteria, for example against susceptible strains of *Staphylococcus aureus, Proteus mirabilis, Escherichia coli, Klebsiella pneumoniae, Enterobacter cloacae* and *Pseudomonas aeruginosa*. The antibacterial material of the invention may further be utilized as an additive to animal feeding-stuffs, for preserving foodstuffs and as a disinfectant. For example, it may be employed in aqueous compositions in concentrations ranging from 0.1 to 100 parts of antibiotic per million parts of solution or preferably in concentrations ranging from about 1 to about 10 parts of antibiotic per million parts of solution in order to destroy and inhibit the growth of harmful bacteria on medical and dental equipment and as bactericides in industrial applications, for example in water-based paints and in the white water of paper mills to inhibit the growth of deleterious bacteria.

The antibiotic of this invention may be used in any one of a variety of pharmaceutical preparations as the sole active ingredient or in combination either with one or more other antibiotics or with one or more pharmacologically active substances. As an example of the former, an aminocyclitol antibiotic such as gentamicin may be coadministered in order to minimize any chance that resistant organisms will emerge. As an example of the latter, diphenoxylate and atropine may be combined in dosage forms intended for the therapy of gastroenteritis. The antibiotic may be employed in capsule form or as tablets, powders or liquid solutions or as suspensions or elixirs. It may be administered orally, topically, intravenously or intramuscularly.

Tablets and capsules for oral administration may be in unit dose presentation form, and may contain conventional excipients such as binding agents, for example, syrup, acacia, gelatin, sorbitol, tragacanth, or polyvinyl-pyrrolidone; fillers, for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible fats; emulsifying agents, for example lecithin, sorbitan monooleate or acacia; nonaqueous vehicles which may include edible oils, for example, almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride.

Compositions for injection may be presented in unit dose form in ampules, or in multidose containers with an added preservative. The compositions may take such forms as suspensions, solutions, emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like.

In veterinary medicine, such as in the treatment of chickens, cows, sheep, pigs and the like, the compositions may, for example, be formulated as intramammary preparations in either long-acting or quick-release bases.

The dosage to be administered depends to a large extent upon the condition of the subject being treated, the weight of the host and the type of infection, the route and frequency of administration, the parenteral route being preferred for generalized infections and the oral route for intestinal infections.

In the treatment of bacterial infections in man, the compound of this invention is administered orally or parenterally, in accordance with conventional procedures for antibiotic administration, in an amount of from about 2 to 600 mg./kg./day and preferably about 5 to 100 mg./kg./day in preferably divided dosage, e.g. three to four times a day. It may be administered in dosage units containing, for example, 25, 250, 330, 400 or 1000 mg. of active ingredient with suitable physiologically acceptable carriers or excipients. The dosage units are in the form of liquid preparations such as solutions or suspensions or as solids in tablets or capsules. It will, of course, be understood that the optimum dose in any given instance will depend upon the type and severity of infection to be treated, and that smaller doses will be employed for pediatric use, all of such adjustments being within the skill of the practitioner in the field.

ASSAY PROCEDURES FOR ANTIBIOTIC 890A$_{10}$

I. Bioassay

An agar plate disc-diffusion method is employed using *Vibrio percolans* ATCC 8461 as tester organism. A purified sample of antibiotic 890A$_1$ is used as standard. Antibiotic 890A$_1$ is prepared according to the procedure set forth in Example 4.

Plates containing *Vibrio percolans* ATCC 8461 are prepared as follows:

A lyophilized culture of *Vibrio percolans* ATCC 8461 is suspended in 15 ml. of a sterilized medium containing 8 g./liter of Difco Nutrient Broth and 2 g./liter of yeast extract in distilled water "nutrient broth-yeast extract" (herein after designated NBYE). The culture is incubated overnight on a rotary shaker at 28° C. This culture is used to inoculate the surface of slants containing 1.5% agar in NBYE, and the inoculated slants are incubated overnight at 28° C., and then stored in a refrigerator.

The refrigerated slants prepared from a single lyophilized culture are used for up to four weeks from their preparation, as follows: A loop of inoculum from the slant is dispersed in 50 ml. of NBYE contained in a 250 ml. Erlenmeyer flask. The culture is incubated overnight on a rotary shaker at 28° C. and then diluted to a density giving 50% transmittance at 660 nm. A 33.2 ml. portion of this diluted culture is added to 1 liter of NBYE containing 15 g. of agar and maintained at 46° C. The inoculated agar-containing medium is poured into 100 × 15 mm. plastic petri dishes, 5 ml. per dish, chilled, and maintained at 2°–4° C. for up to 5 days before using.

Filter paper discs of one-half inch diameter are dipped into the solution to be assayed, and are placed on the agar. Alternatively, the discs may be loaded by pipetting one-tenth ml. of solution onto a dry disc, and then placing the disc on the agar. The diameter of the zone of inhibition is measured after appropriate incubation (12–24 hours at 25° C.). If necessary, dilutions of the solutions to be assayed are made in 0.05 M potassium phosphate buffer, pH 7.4 "potassium phosphate buffer" (hereinafter referred to as KPB), or in deionized water.

Calculations of potencies proceed as follows: a slope is determined by measuring the zone diameters of a solution of antibiotic $890A_{10}$ and of a fourfold dilution (in KPB) of this solution. Two discs of each concentration are assayed on a single plate, and the average zone size at each concentration is determined. The slope is equal to one-half of the difference of the average zone sizes. Potencies are then calculated by the formula:

$$\text{Potency (units/ml.)} = \left( \frac{[D - D_s] \log 2}{\text{slope}} \right)$$
$$(\text{Potency of Standard}) \times \text{Dilution} \times 10$$

where D is the average diameter of the zones formed by the unknown, $D_s$ is the average diameter of the standard zones, and "Dilution" is the degree to which the unknown was diluted before assay. If no standard is used, $D_s$ is assumed to be 25 mm. and (Potency of Standard) is taken as 1 unit/ml., when measured on *Vibrio percolans* ATCC 8461. Pure $890A_1$ is defined as having a potency of 250 units per hydroxylamine-extinguishable absorbance unit at 300 nm, when used as a standard.

II. Assay Procedure for Determining "890 Assay Units"

A conventional agar plate disc-diffusion method is employed using *Vibrio percolans* ATCC 8461 as tester organism. Cephaloridine is employed as a standard. Plates containing *Vibrio percolans* ATCC 8461 are prepared as follows. A culture of *Vibrio percolans* ATCC 8461 is incubated in nutrient broth-yeast extract overnight on a rotary shaker at 28° C. and then diluted to a density of 60% transmittance at 660 nm. A 33.2 ml. portion of this diluted culture is added to 1 liter of a medium composed of nutrient agar plus 0.2% yeast extract maintained at 46° C. The inoculated agar-containing medium is poured into 100×15 mm. plastic-petri dishes, 10 ml. per dish, chilled, and maintained at 2°–4° C. for up to 5 days before use.

The concentration of cephaloridine which is equivalent to 1 unit/ml. of $890A_1$ is determined by assay on plates prepared as above, but containing 5 ml. of inoculated medium per plate, as follows. Four concentrations of cephaloridine constitute the standard—3.12, 6.25, 12.5 and 25 mcg per ml. with the 12.5 mcg per ml. as a reference solution. The zone diameters on a 5 ml. plate for the standard are as follows:

| Conc. (mcg/ml.) | Zone Diameter (mm.) |
| --- | --- |
| 3.12 | 16.8 |
| 6.25 | 22.3 |
| 12.5 | 25.0 |
| 25 | 29.6 |

A unit is defined as the amount of antibiotic per ml. producing a 25 mm. zone of inhibition on a 5 ml. plate as described in section I above. Therefore, in this assay a concentration of 12.5 mcg per ml. of cephaloridine is considered equivalent to 1 unit of $890A_1$ per ml. Since the slope of the line for cephaloridine is 4.0 calculations of the potency of a sample are made using a slope of 4.0.

III. Hydroxylamine Reaction

Antibiotic $890A_{10}$ reacts with hydroxylamine and produces a substance with greatly diminished absorbance at 300 nm. This provides the basis for a quantitative assay of the antibiotic $890A_{10}$.

The solution to be assayed is brought to 0.05 M in potassium phosphate, pH 7.4 by adding 1/20th volume of a solution containing 0.8 M $K_2HPO_4$ and 0.2 M $KH_2PO_4$. Then one-hundredth volume of 1 M hydroxylamine hydrochloride is added, and the absorbance at 300 nm is measured at intervals of one-half to two minutes. The reaction is conducted at room temperature. First-order kinetics are assumed and a half-life is estimated from the absorbance decrease during the first ten minutes. From this half-life, the time is estimated beyond which no further absorbance decrease should be observed and observations are continued beyond that time. If no further decrease is observed beyond that time, the total absorbance decrease (correcting for dilution effect and absorbance of the hydroxylamine) is taken as the "Hydroxylamine-extinguishable absorbance at 300 nm ($HAEA_{300}$)". If absorbance decrease is observed beyond that time, the rate of background absorbance decrease is calculated, and the observed decrease at that time is corrected for background decrease, assuming that background decrease is linear with time. The corrected value is then recorded as the $HAEA_{300}$.

The number of $HAEA_{300}$ units is equal to the $HAEA_{300}$ multiplied by the volume in ml.

The examples which follow illustrate the methods by which the products of this invention may be obtained. However, the examples are illustrative only and it should be apparent to one having ordinary skill in the art that this invention includes the functionally equivalent products and methods for their preparation. Therefore, any modification of the processes described herein which results in the formation of the products of this invention should be construed as constituting an analogous method. The described processes are capable of wide variation and modification and any minor departure or extension is considered as being within the skill of the artisan and as falling within the scope of this invention.

EXAMPLE 1

Method of Isolation of N-Acetyl-$890A_{10}$ amidohydrolase-producing Organisms

A 1% (w/v) suspension of fertile lawn soil is prepared by suspending 1 g. of lawn soil in 100 ml. sterile phosphate buffer-saline solution wherein the phosphate buffer-saline solution has the following composition:

| Phosphate Buffer-Saline Solution | |
| --- | --- |
| NaCl | 8.8 g. |
| 1M Phosphate Buffer, pH 7.5* | 10 ml. |
| Distilled $H_2O$ | 1000 ml. |

*1M Phosphate Buffer, pH 7.5
16 ml. 1M $KH_2PO_4$ are mixed with 84 ml. 1M $K_2HPO_4$. The pH of the phosphate buffer is adjusted to 7.5 by adding small quantities of either 1M $KH_2PO_4$ or 1M $K_2HPO_4$.

Aliquots of this 1% stock soil suspension are used to prepare 10×, 100× and 1,000× dilutions.

One-ml. portions of the stock suspension or 1-ml. portions of the 10×, 100× and 1,000× dilutions are added to 2-ml. portions of sterile, 1.0% agar solutions at 48° C. The mixtures are quickly poured over the surface of sterile petri dishes of 85 mm. diameter containing 20 ml. of Medium A. Medium A has the following composition:

| Medium A | |
|---|---|
| $KH_2PO_4$ | 3.0 g. |
| $K_2HPO_4$ | 7.0 g. |
| $MgSO_4$ | 0.1 g. |
| Distilled $H_2O$ | 1000 ml. |
| N-Acetylethanol-amine solution* | 8.5 ml. |

*N-acetylethanolamine Solution
N-acetylethanolamine is diluted 10× in $H_2O$ and membrane sterilized. This solution is added after autoclaving.
For solid media: Add 20 g. agar The petri dishes are incubated for 18 days at 28° C. Well-isolated colonies are picked and streaked on Medium B. Medium B has the following composition:

| Medium B | |
|---|---|
| Tomato Paste | 40 g. |
| Ground Oatmeal | 15 g. |
| Distilled $H_2O$ | 1000 ml. |
| pH adjusted to 6 using NaOH | |

For solid media: add 20 g. agar

Individual clones are selected and grown for two days at 28° C. on slants of Medium B.

A portion of the growth of the slants is used to inoculate a 250-ml. Erlenmeyer flask containing 50 ml. of Medium A; a 250-ml. Erlenmeyer flask containing 50 ml. supplemented Medium B (supplemented after autoclaving with 0.4 ml. of a membrane-sterilized solution of N-acetylethanolamine diluted 10× with water); and a 250-ml. Erlenmeyer flask containing 50 ml. Medium C. Medium C has the following composition:

| Medium C | |
|---|---|
| Dextrose | 20 g. |
| Pharmamedia | 8 g. |
| Corn Steep Liquor (wet basis) | 5 g. |
| Distilled $H_2O$ | 1000 ml. |
| pH adjusted to 7 with NaOH or HCl | |
| N-acetylethanol-amine solution* | 8.5 ml. |

*N-acetylethanolamine Solution
N-acetylethanolamine is diluted 10 × in $H_2O$ and membrane sterilized. This solution is added after autoclaving.

The flasks are shaken at 28° C. on a 220 rpm (2" throw) shaker for 4 days. A 30 ml. portion from each flask is centrifuged for 15 minutes at 8,000 rpm. The supernatant portion is removed, leaving only enough to form a thick suspension of cells and media solids. Half of the suspension is subjected to ultrasonic disruption using a Branson Instrument Model LS-75 Sonifier with a ½ inch probe. The input power is set at position No. 4, and four successive 15 second cycles of irradiation are used, while chilling the suspension in ice water during and between disruption. To test for the presence of N-acetyl-890$A_{10}$ amidohydrolase activity, a 10-μl. portion of the sonicate is mixed with 25 μl. of an 890$A_{10}$ solution containing 500 μg. per ml. Controls containing antibiotic and buffer alone; and sonicated cells and buffer without antibiotic are also run. After incubation overnight at 28° C., 10 μl. quantities are applied to Schleicher and Schuell No. 2043-B paper. Using 0.03 M potassium phosphate buffer pH 7.1, a voltage gradient of 50 volts/cm. is applied for 30 minutes. The paper is placed on a *Staphylococcus aureus* ATCC 6538P plate and incubated at 37° C. for 18 hours.

The assay plates are prepared as follows: an overnight growth of the assay organism, *Staphylococcus aureus* ATCC 6538P, in nutrient broth plus 0.2% yeast extract is diluted with nutrient broth, plus 0.2% yeast extract to a suspension having 60% transmittance at a wavelength of 660 nm. This suspension is added to Difco nutrient agar supplemented with 2.0 g./l. Difco yeast extract at 47° C. to 48° C., to make a composition containing 33.2 ml. of the suspension per liter of agar. Forty ml. of this suspension is poured into 22.5 cm.×22.5 cm. petri plates, and these plates are chilled and held at 4° C. until used (5 day maximum).

The unchanged bioactive 890$A_{10}$ spot migrated 8 cm. toward the positive pole. A new bioactive spot due to desacetyl 890$A_{10}$ is detected and migrated 4 cm. toward the positive pole. Control incubation mixtures of antibiotic plus buffer, and cell sonicate plus buffer produce no bioactive material migrating 4 cm. toward the positive pole.

EXAMPLE 2

Deacetylation of 890$A_{10}$

A portion of the growth on a slant of *Protaminobacter ruber* MB-3528 is used to inoculate a 250-ml. Erlenmeyer flask containing 50 ml. of Medium C. Medium C has the following composition:

| Medium C | |
|---|---|
| Dextrose | 20 g. |
| Pharmamedia | 8 g. |
| Corn Steep Liquor (wet basis) | 5 g. |
| Distilled $H_2O$ | 1000 ml. |
| pH adjusted to 7 with NaOH or HCl | |
| N-acetylethanolamine solution* | 8.5 ml. |

*N-acetylethanolamine Solution
N-acetylethanolamine is diluted 10 × in $H_2O$ and membrane sterilized. This solution is added after autoclaving.

The flask is shaken at 28° C. on a 220 rpm (2-inch throw) shaker for four days. A 25-ml. portion from the flask is centrifuged for 15 minutes at 8,000 rpm. The supernatant is removed and the cells on the surface of the media solids scraped off into 0.5 ml. of 0.05 M potassium phosphate buffer, pH 7.4. The resulting suspension is subjected to ultrasonic disruption using a Branson Instrument Model LS-75 Sonifier with a ½-inch probe at setting 4 for four, 15-second intervals, while chilling the suspension in ice water during and between disruption. A 10-μl. portion of the sonicate is mixed with 25 μl. of an 890$A_{10}$ solution containing 500 μg. per ml. Controls containing antibiotic and buffer alone; and sonicated cells and buffer without antibiotic are also run. After incubation overnight at 28° C., 10-μl. quantities are applied to Schleicher & Schuell No. 2043-B paper. Using 0.03 M potassium phosphate buffer, pH 7.1, a voltage gradient of 50 volts/cm. is applied for 30 minutes. The paper is placed on a *Staphylococcus aureus* ATCC 6538P assay plate and incubated at 37° C. for 18 hours.

The assay plates are prepared as follows: an overnight growth of the assay organism, *Staphylococcus aureus* ATCC 6538P, in nutrient broth plus 0.2% yeast extract is diluted with nutrient broth, plus 0.2% yeast extract to a susupension having 60% transmittance at a wavelength of 660 nm. This suspension is added to Difco nutrient agar supplemented with 2.0 g./l. Difco yeast extract at 47° C. to 48° C., to make a composition containing 33.2 ml. of the suspension per liter of agar. Forty ml. of this suspension is poured into 22.5 cm.×22.5 cm. petri plates, and these plates are chilled and held at 4° C. until used (5 day maximum).

In addition to the unchanged bioactive $890A_{10}$ spot migrating 8 cm. toward the positive pole, a new bioactive spot due to desacetyl $890A_{10}$ is found migrating 4 cm. toward the positive pole. Control incubation mixtures of antibiotic plus buffer, and cell sonicate plus buffer produce no bioactive material migrating 4 cm. toward the positive pole.

EXAMPLE 3

Preparation of Antibiotic $890A_{10}$

Two frozen vials each containing 2 ml. of MA-4638 inoculum are slowly thawed, and the contents aseptically transferred to two seed flasks each containing 500 ml. of C Medium. The seed flask, 2-liter, triple-baffled shake flask equipped with a side arm, is stoppered with cotton.

| C Medium | |
|---|---|
| Autolyzed Yeast (Ardamine*) | 10.0 g. |
| Glucose | 10.0 g. |
| MgSO$_4$ . 7H$_2$O | 0.05 g. |
| Phosphate Buffer** | 2.0 ml. |
| Distilled Water | 1000 ml. |
| pH adjusted to 6.5 with | |
| NaOH before sterilization | |

*Ardamine: Yeast Products, Inc.
**Phosphate buffer solution:

| | |
|---|---|
| KH$_2$PO$_4$ | 91.0 g. |
| Na$_2$HPO$_4$ | 95.0 g. |
| Distilled Water | 1000 ml. |

The inoculated seed flasks are shaken for 24–30 hours at 28° C.±1° C. on a 210 rpm gyrotory shaker, 2-inch throw.

The growth from the seed flasks are used to inoculate two 14-liter glass fermentors containing 10 liters of production medium (D medium plus 0.15% soybean oil, v/v).

| D Medium | |
|---|---|
| Dextrin (CPC Modified Starch) | 40.0 g. |
| Distiller's Solubles | 7.0 g. |
| Yeast Extract | 5.0 g. |
| CoCl$_2$ . 6H$_2$O | 50.0 mg. |
| Distilled Water | 1000 ml. |
| pH adjusted to 7.3 with | |
| NaOH before sterilization | |

The fermentors are operated at 24° C. using an agitation rate of 640 rpm (about Kd 5.5), and an air flow of 0.5 VVM, for 72 hours. Defoamer, Hodag-MF (Hodag Chemical Corp.) is used as required, but not to exceed 0.1%.

Contents of the two fermentors are pooled after the fermentation run, about 20 liters.

200-Ml. portions of the batch are centrifuged in a Servall RC-2B centrifuge at 9000 rpm for 20 minutes. The supernatant is filtered through a 1 cm. bed of Hyflo Super-Cel in a 13-inch Lapp funnel with a cloth filter. The filtrate has a bioactivity of 20 units/ml.

The filtered broth, (18 liters) is applied to a column (8.2×29 cm.) of Dowex-1×2(Cl$^-$) 50–100 mesh, at 150 ml./min. The column is then washed with 1 liter of deionized water followed by 15 liters of 0.15 M NaCl+0.01 M Tris-HCl buffer, pH 7.0+25 $\mu$M neutral EDTA in 50% MeOH at 150 ml./min.

The antibiotic $890A_{10}$ is then eluted with 3.2% NaCl+0.02 M Tris-HCl buffer pH 7.0+25 $\mu$M neutral EDTA in 80% MeOH at 100 ml./min. Fractions are collected as follows: one fraction of 1 liter, four fractions of 500 ml. each, and twelve fractions of 1 liter each are collected. Bioactivity and absorbance at 220 nm is measured on each fraction, and those fractions leaving bioactivity/$A_{220}$ ratios of greater than 0.6 units/$A_{220}$ unit, and which also contained more than 10% of the total recovered activity per fraction are combined for further purification. Thus, fractions 4 through 8 are combined, containing a total of 22% of the applied bioactivity.

The pooled fractions are concentrated under reduced pressure to 190 ml., the precipitated salt is washed with deionized water, and the wash is added to the supernatant, bringing the final volume to 220 ml. The concentrate is adjusted to pH 6.5 with HCl and is applied on a column (6.0×59 cm.) of Amberlite XAD-2 which has been previously washed with 8 liters of 60% aqueous acetone followed by 16 liters of deionized water. After application is completed, the column is rinsed with 5×10 ml. portions of deionized water, and the antibiotics are eluted with deionized water at 35 ml./min. Fractions are collected as follows: one fraction of 500 ml. followed by seven fractions of 250 ml. each, followed by four fractions of 500 ml.

Bioactivity and $HAEA_{304}$ values are measured on fractions from 3 through 12. Fractions 4 through 9 have $HAEA_{304}/A_{220}$ ratios greater than 0.01, and are combined for further purification. Fraction 3, containing about one-fifth of the applied salt, is also added to this pool. The combined pool contains 469 $HAEA_{304}$ units.

The pooled fractions are diluted to 4.1 liters and are applied to a column (2.15×42 cm.) of Dowex-1×4(Cl$^-$) minus 400 mesh at 2 ml./min. The column is washed with 100 ml. of 50% methanol, and the antibiotic is eluted with 0.25 M NaCl+0.01 M NH$_4$Cl+0.0001 M NH$_3$ in 80% MeOH at approximately 2 ml./min. Fractions of from 8 to 12 ml. are collected.

The bioactivity and the absorbance at 220 nm, 260 nm, and 300 nm are measured for every fifth fraction, and $HAEA_{300}$ is measured on the peak bioactive fractions. The $890A_{10}$ bioactivity appears in fractions 85 through 150, with a maximum at fraction 120. Fractions with $HAEA_{300}/A_{300}$ values greater than 0.05 are combined for further purification. Thus, fractions 105 through 133 are combined, containing a total of 130 $HAEA_{300}$ units. The pooled fractions 105 through 133 are diluted to 1900 ml. with deionized water, and the pH is adjusted to 7.6. The sample is applied to a column (2.15×42 cm.) of Dowex-1×2(Cl$^-$), minus 400 mesh, which has been previously washed with 3 liters of 3% NaCl in 50% methanol followed by 50 ml. of 50% methanol. After the entire sample has been applied, the column is washed with 100 ml. of 30% methanol, and is eluted at 2 ml./min. with 0.26 M NaCl+0.005 M $NH_4Cl + 0.0002$ M $NH_3$ in 30% methanol. Fractions of 10 to 12 ml. are collected.

The main peak of antibiotic $890A_{10}$ appears in fractions 230 to 290, with a maximum at fraction 260. Those fractions with an $A_{300}/A_{250}$ ratio greater than 1.10 and an $A_{300}/A_{220}$ ratio greater than 0.83 are combined for further purification. Thus, fractions 240 through 275 are combined, containing 91.6 $HAEA_{300}$ units.

The combined fractions 240 through 275 are concentrated under reduced pressure to 10 ml., and the concentrate is separated from the precipitated salt by pipetting. The salt is washed with 2 ml. deionized water, and the wash is added to the concentrate. The combined 12 ml. of concentrate and wash is applied to a column (2.15×76 cm.) of Bio-Gel P-2 (200–400 mesh), which has been previously washed with 30 ml. of saturated NaCl in deionized water, followed by 1500 ml. of deionized water and 50 ml. of 0.05 $mMNH_3$ in deionized water. After application is complete, the column is rinsed with 3×1 ml. rinses of 0.05 $mMNH_3$ in deionized water, and the antibiotic is eluted with 0.05 $mMNH_3$ in deionized water at 0.73 ml./min. Fractions of 3.65 ml. each are collected.

The main peak of antibiotic $890A_{10}$ appears in fractions 29 through 50, with a maximum at fraction 36. Those fractions having an $A_{300}/A_{250}$ ratio greater than 1.9, and also having an $A_{300}/A_{220}$ ratio greater than 1.45, are combined for lyophilization and NMR analysis. Thus, fractions 36 through 45 are combined, containing 50.8 $A_{300}$ units, of which 45.1 is hydroxylamine-extinguishable.

The combined fractions 36 through 45 are concentrated under reduced pressure to 1 ml., and 5 ml. $D_2O$ are added. The sample is again concentrated to 0.835 ml., and 0.825 ml. of this is transferred to a glass vial and freeze-dried and lyophilized. The lyophilized sample contains 48.2 $A_{300}$ units and has 4.6 mg. of solids.

EXAMPLE 4

Preparation of Antibiotic $890A_1$

A tube of lyophilized culture of *Streptomyces flavogriseus* MA-4600a is aseptically opened and the contents suspended in a tube containing 1.5 ml. of sterile medium A having the following composition:

| Medium A | |
|---|---|
| Yeast Extract | 10.0 g. |
| Glucose | 10.0 g. |
| $MgSO_4 \cdot 7H_2O$ | 0.05 g. |
| *Phosphate Buffer | 2 ml. |
| Distilled $H_2O$ | 1000 ml. |
| *Phosphate Buffer Solution | |
| $KH_2PO_4$ | 91.0 g. |
| $Na_2HPO_4$ | 95.0 g. |
| Distilled $H_2O$ | 1000 ml. |

This suspension is used to inoculate a 250-ml. triple-baffled Erlenmeyer seed flask containing 54 ml. of seed medium B having the following composition:

| Medium B | |
|---|---|
| Autolyzed Yeast (Ardamine+) | 10.0 g. |
| Glucose | 10.0 g. |
| $MgSO_4 \cdot 7H_2O$ | 0.05 g. |
| *Phosphate Buffer | 2 ml. |
| Distilled $H_2O$ | 1000 ml. |
| pH adjusted to 6.5 with NaOH | |

†Ardamine: Yeast Products Corporation
*Phosphate Buffer Solution

| | |
|---|---|
| $KH_2PO_4$ | 91.0 g. |
| $Na_2HPO_4$ | 95.0 g. |
| Distilled $H_2O$ | 1000 ml. |

The seed flask is stoppered with cotton and shaken for 30 hours at 28° C.±1° C. on a 220 rpm gyrotory shaker (2-inch throw).

Fifty 250-ml. unbaffled Erlenmeyer production flasks, each containing 40 ml. of production medium C are inoculated with 1 ml. per flask of the broth from the seed flask. The production flasks are stoppered with cotton.

| Medium C | |
|---|---|
| Tomato Paste | 20.0 g. |
| Primary Yeast | 10.0 g. |
| Dextrin (Amidex) | 20.0 g. |
| $CoCl_2 \cdot 6H_2O$ | 5.0 mg. |
| Distilled $H_2O$ | 1000 ml. |
| pH adjusted to 7.2–7.4 with NaOH | |

After inoculation, the production flasks are incubated at 28° C.±1° C. with shaking on a 220 rpm gyrotory shaker (2-inch throw) for three days. The flasks are assayed for activity against standard *Vibrio percolans* ATCC 8461 assay plates using ¼ inch assay discs dipped into centrifuged fermentation broth samples. Samples are diluted with 0.05 M phosphate buffer, pH 7.4. The results are tabulated below:

| | |
|---|---|
| Harvest Age Hours | 72 |
| pH | 6.4 |
| *Vibrio percolans* | |
| (1/100 Dilution) Assay | 23 mm. |
| 890 Assay, units/ml. | 103 |

The whole broth is centrifuged in 200-ml. portions in polycarbonate bottles at 9000 rpm for 15 minutes to give 1600 ml. of combined supernatants with a potency of 104 units/ml. To this is added 0.5 ml. of neutral EDTA.

The centrifuged broth is adsorbed on a Dowex-1×2 ($Cl^-$), 50–100 mesh column, bed dimensions 3.8×22 cm., at a flow rate of 6 to 20 ml./min. The column is rinsed with 100 ml. of deionized water and eluted with 1 liter of deionized water containing 50 g. of sodium chloride, 0.02 M Tris HCl buffer, pH 7.0, and 25 $\mu$M neutral EDTA, at a flow rate of 6 ml./min. Fractions of 10 ml. are collected.

Antibiotic $890A_1$ appears in fractions 13 through 81, with a maximum at fractions 25 to 33, counting from the first application of salt eluate. Fractions 24 through 41, having the highest biopotency/$A_{200}$ ratios, are combined for further processing. The combined fractions have a total of 29,000 units, or 17% of the applied bioactivity.

The Dowex eluate is concentrated to 10 ml., the pH is adjusted to 6.5 with dilute hydrochloric acid, and the concentrate is applied on a column of XAD-2, bed dimensions 3.3×36 cm., which had been previously washed with 2 liters each of 60% aqueous acetone, deionized water, and 5% (w/v) sodium chloride in deionized water. The sample is eluted with deionized water at a flow rate of 6 ml./min. Fractions of 40 to 260 ml. are collected.

Antibiotic activity appears in fractions 6 through 14, extending from 220 to 2560 ml. of eluted volume. The peak is at fractions 9 and 10, extending from 370 to 590 ml. of eluted volume. Fractions 9 through 12, extending from 370 to 1060 ml. of eluted volume, have the highest ratios of $HAEA_{300}/A_{220}$, and are combined for further processing. These fractions have 36,600 units, equal to 126% of the apparent applied activity.

The combined fractions 9 through 12 are concentrated to 100 ml. and the concentrate applied on a column of Dowex-1×4 (Cl$^-$), minus 400 mesh, bed dimensions 2.2×41 cm., at a flow rate of 2 ml./min. The column is rinsed with 50 ml. of deionized water, and eluted with 3 liters of 0.07 M $NaCl+0.005$ M $NH_4Cl+0.0001$ M $NH_3$ in deionized water, at a rate of 2 ml./min. Fractions of 10.8 ml. are collected, starting from the first application of eluent.

The main peak of antibiotic $890A_1$ appears in fractions 181 through 217, with a maximum at fraction 198. Fractions 186 through 210, containing a total of 114 absorption units at 300 nm., are pooled.

The pooled fractions are concentrated to 4.0 ml., and the pH is adjusted to 7.3 by addition of 16 μliter of 1 M NaOH. The concentrate is applied on a column of Bio-Gel P-2, 200–400 mesh, bed dimension 2.15×70 cm., and is washed in with 3×1 ml. washes of deionized water and eluted with deionized water at 0.96 ml./min. Fractions of 3.85 ml. are collected.

The main peak of antibiotic $890A_1$ appears in fractions 24 through 44, with a maximum at fractions 33 and 34. Fractions 27 through 38, having the highest $A_{300}/A_{245}$ ratios, are combined for lyophilization. These combined fractions have a total of 72 $A_{300}$ units.

To carry out the lyophilization, the combined fractions are concentrated to 3.0 ml. and the pH of the concentrate is adjusted to 7.5 by addition of 10 μliters of 0.1 M NaOH. The sample is divided into two portions of 1.50 ml. each, and the portions are separately quick-frozen and lyophilized from 14 ml. glass screw-cap vials. Each sample contains 1.73 mg. of $890A_1$, corresponding to 35.8 $A_{300}$ units.

A culture of *Streptomyces flavogriseus* designated MA-4600a in the MERCK & CO., Inc. culture collection has been placed on permanent deposit without restrictions as to availability with the culture collection of the Northern Regional Laboratories, Northern Utilization Research and Development Division, Agricultural Research Service, U.S. Department of Agriculture, Peoria, Ill. and is available to the public under accession No. NRRL 8140.

What is claimed is:

1. A process for producing the compound desacetyl $890A_{10}$ having the structure:

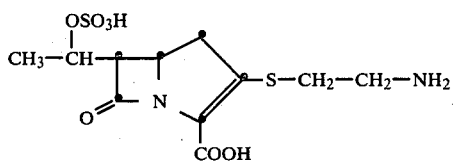

which comprises intimately contacting the compound $890A_{10}$ having the structure:

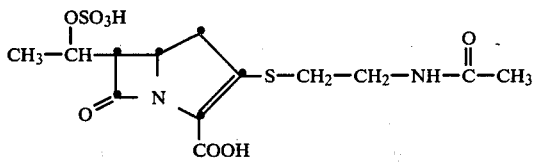

with the enzyme N-acetyl-$890A_{10}$ amidohydrolase produced by an amidohydrolase-producing strain of the microorganism *Protaminobacter ruber*.

2. The process of claim 1 wherein the microorganism is *Protaminobacter ruber* NRRL B-8143.

* * * * *